United States Patent [19]

Stach et al.

[11] 4,398,938
[45] Aug. 16, 1983

[54] N-ACYLATED LACTAMS AND THEIR HERBICIDAL COMPOSITIONS AND METHOD OF USE

[75] Inventors: Leonard J. Stach, Riverside; Frank Wu, Libertyville, both of Ill.

[73] Assignee: Velsicol Chemical Corporation, Chicago, Ill.

[21] Appl. No.: 379,839

[22] Filed: May 20, 1982

[51] Int. Cl.³ .................... A01N 43/46; C07D 223/10
[52] U.S. Cl. .......................................... 71/88; 71/94; 71/95; 260/239.3 R; 546/221; 548/539
[58] Field of Search ................. 260/239.3 R; 546/221; 548/539; 71/88, 94, 95

[56] References Cited
U.S. PATENT DOCUMENTS
4,369,139  1/1983  Kyburz et al. ...................... 548/539

Primary Examiner—Robert T. Bond
Attorney, Agent, or Firm—Robert J. Schwarz

[57] ABSTRACT

This invention relates to compounds of the formula:

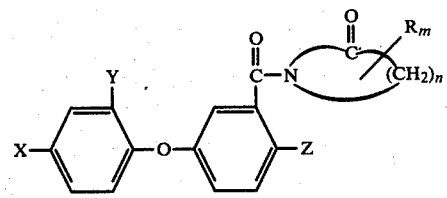

wherein X is halogen or trifluoromethyl; hydrogen, halogen or cyano; Z is halogen, cyano or nitro; R is alkyl; m is an integer from 0 to 6; and n is an integer from 3 to 5.

12 Claims, No Drawings

N-ACYLATED LACTAMS AND THEIR HERBICIDAL COMPOSITIONS AND METHOD OF USE

This invention relates to new compositions of matter. In particular, this invention relates to new chemical compounds of the formula:

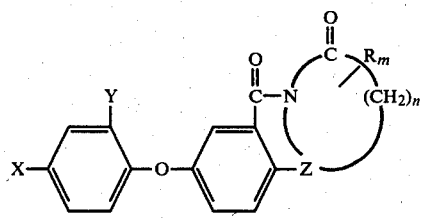

wherein X is halogen or trifluoromethyl; Y is hydrogen, halogen or cyano; Z is halogen, cyano or nitro; R is alkyl; m is an integer from 0 to 6 and n is an integer from 3 to 5.

The compounds of the present invention are unexpectedly useful as herbicides.

In the preferred embodiment of this invention, X is trifluoromethyl; Y is hydrogen or chlorine; Z is nitro and m is 0.

The compounds of the present invention can be readily prepared by reacting a compound of the formula:

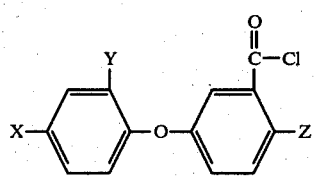

with a compound of the formula:

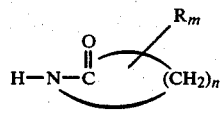

wherein R, X, Y, Z, m and n are as heretobefore described.

This reaction proceeds without heating in the presence of an acid scavenger for the hydrogen chloride by-product such as triethylamine, potassium hydroxide, sodium carbonate or the like and in an aromatic solvent such as toluene, xylene or a ketone. The desired product can be recovered by standard procedures such as extraction or distillation and purified by conventional means such as chromatography.

EXAMPLE 1

Preparation of
1-[3-(2-Chloro-4-Trifluoromethylphenoxy)-6-Nitrobenzoyl] Hexamethylenimin-2-one Hexamethylenimin-2-one (2.26 grams; 0.02 mol), triethylamine (2.0 grams; 0.02 mol) and toluene (50 ml) were placed in a three-necked, glass reaction flask equipped with stirrer, thermometer, addition funnel and drying tube. 3-(2-Chloro-4-trifluoromethylphenoxy)-6-nitrobenzoylchloride (7.60 grams; 0.02 mol) in toluene (10 ml) was added to the mixture in the flask. The mixture, after being stirred overnight at room temperature, was washed with water, dried over sodium sulfate and evaporated resulting in a dark oil. Then the product was chromatographed with silica gel to give three fractions; the first two fractions obtained from using toluene as eluant and the third from using an equal mixture of ethyl acetate and toluene gave the desired product as a yellow oil. It analyzed as follows:

|  | C | H | N |
|---|---|---|---|
| Calculated: | 52.58 | 3.53 | 6.13 |
| Found: | 52.52 | 3.59 | 6.09 |

EXAMPLE 2

Preparation of
1-[3-(2-Chloro-4-Trifluoromethylphenoxy)-6-Nitrobenzoyl] Pyrrolidin-2-one Pyrrolidin-2-one (7.60 grams; 0.02 mol), triethylamine (2.0 grams; 0.02 mol) and toluene (50 mol) were placed in a three-necked, glass reaction flask equipped with stirrer, thermometer, addition funnel and drying tube. 3-(2-Chloro-4-trifluoromethylphenoxy)-6-nitrobenzoylchloride (7.60 grams; 0.02 mol) in toluene (10 ml) was added to the mixture in the flask. The mixture, after being stirred overnight at room temperature, was washed with water, dried over sodium sulfate and evaporated to give a dark oil. The oil was chromatographed using silica gel into two fractions, the first using toluene as eluant and the second fraction using an equal mixture of toluene and ethyl acetate gave the desired product as a brown oil which solidified upon standing. Trituration with isopropyl ether resulted in white crystals, melting point 88° C. This product analyzed as follows:

|  | C | H | N |
|---|---|---|---|
| Calculated: | 50.42 | 2.82 | 6.53 |
| Found: | 50.34 | 2.82 | 6.52 |

EXAMPLE 3

Preparation of
1-]3-(2-Chloro-4-Trifluoromethylphenoxy)-6-Nitrobenzoyl] Piperidin-2-one Piperidin-2-one (1.98 grams; 0.02 mol), triethylamine (2.0 grams; 0.02 mol) and toluene (50 ml) were placed in a three-necked, glass reaction flask equipped with stirrer, thermometer, addition funnel and drying tube. 3-(2-Chloro-4-trifluoromethylphenoxy)-6-nitrobenzoylchloride (7.60 grams; 0.02 mol) in toluene (10 ml) was added to the mixture in the flask. The mixture, after being stirred overnight at room temperature, was washed with water, dried over sodium sulfate, and evaporated to give a dark oil. The oil was chromatographed over silica gel into two fractions, the first using toluene as eluant and the second fraction using an equal mixture of toluene and ethyl acetate gave the product as a brown oil. This product analyzed as follows:

|  | C | H | N |
|---|---|---|---|
| Calculated: | 51.54 | 3.19 | 6.33 |

-continued

| | C | H | N |
|---|---|---|---|
| Found: | 51.46 | 3.18 | 6.22 |

Exemplary of the compounds within the scope of the present invention that can be prepared by the procedures of the preceding examples are:

1-[3-(2,4-Dichlorophenoxy)-6-Nitrobenzoyl] Piperidin-2-one

1-[3-(4-Trifluoromethylphenoxy)-6-Nitrobenzoyl] Pyrrolidin-2-one

1-[3-(2,4-Dibromophenoxy)-6-Cyanobenzoyl] Hexamethyleneimin-2-one

1-[3-(2-Cyano-4-Trifluoromethylphenoxy)-6-Bromobenzoyl] Pyrrolidin-2-one

1-[3-(2,4-Diiodophenoxy)-6-Iodobenzoyl] Hexamethyleneimin-2-one

1-[3-(2-Chloro-4-Bromophenoxy)-6-Nitrobenzoyl] Piperidin-2-one

1-[3-(2-Fluoro-4-Iodophenoxy)-6-Cyanobenzoyl] Hexamethyleneimin-2-one

1-[3-(2-Cyano-4-Bromophenoxy)-6-Chlorobenzoyl] Piperidin-2-one

1-[3-(2-Iodo-4-Trifluoromethoxyphenoxy)-6-Nitrobenzoyl] Pyrrolidin-2-one

1-[3-(2-Bromo-4-Chlorophenoxy)-6-Iodobenzoyl] Piperidin-2-one

1-[3-(2,4-Difluorophenoxy)-6-Fluorobenzoyl] Hexamethyleneimin-2-one

1-[3-(2-Fluoro-4-Trifluoromethylphenoxy)-6-Iodobenzoyl] Pyrrolidin-2-one

1-[3-(2,4-Dibromophenoxy)-6-Bromobenzoyl] 3,4,5,6-Tetramethyl Hexamethyleneimin-2-one 1-[3-(2-Bromo-4-Trifluoromethylphenoxy)-6-Bromobenzoyl] 3,4,5-Triethyl Pyrrolidin-2-one 1-[3-(2-Chloro-4-Trifluoromethylphenoxy)6-Iodobenzoyl] 3,3,4,4-Tetrabutyl Piperidin-2-one 1-[3-(2-Cyano-4-Chlorophenoxy)-6-Chlorobenzoyl] 3-Ethyl-5-Pentylhexamethyleneimin-2-one 1-[3-(2-Iodo-4-Iodophenoxy)-6-Iodobenzoyl] 3,4-Dipropylpyrrolidin-2-one 1-[3-(2,4-Diiodophenoxy)-6-Nitrobenzoyl] 3,3,4,5,6,6-Hexamethylpiperidin-2-one 1-[3-(4-Bromophenoxy)-6-Chlorobenzoyl] 3,4,7-Trihexylhexamethyleneimin-2-one 1-[3-(2-Chloro-4-Trifluoromethylphenoxy)-6-Nitrobenzoyl] 4-Ethyl-5-Propylhexamethyleneimin-2-one 1-[3-(4-Trifluoromethylphenoxy)-6-Bromobenzoyl] 5-Butylpyrrolidin-2-one 1-[3-(2-Bromo-4-Chlorophenoxy)-6-Chlorobenzoyl] 4,5,6-Triisopropylpiperidin-2-one 1-[3-(2-Iodo-4-Bromophenoxy)-6-Nitrobenzoyl] 3,3,4,4,5,5-Hexaethylpyrrolidin-2-one 1-[3-(2-Fluoro-4-Bromophenoxy)-6-Iodobenzoyl] 3-Methyl 4-Ethylpiperidin-2-one For practical use as herbicides the compounds of this invention are generally incorporated into herbicidal compositions which comprise an inert carrier and a herbicidally toxic amount of such a compound. Such herbicidal compositions, which can also be called formulations, enable the active compound to be applied conveniently to the site of the weed infestation in any desired quantity. These compositions can be solids such as dusts, granules, or wettable powders; or they can be liquids such as solutions, aerosols or emulsifiable concentrates.

For example, dusts can be prepared by grinding and blending the active compound with a solid inert carrier such as the talcs, clays, silicas, pyrophyllite, and the like. Granular formulations can be prepared by impregnating the compound, usually dissolved in a suitable solvent, onto and into granulated carriers such as the attapulgites or the vermiculites, usually of a particle size range of from about 0.3 to 1.5 mm. Wettable powders, which can be dispersed in water or oil to any desired concentration of the active compound, can be prepared by incorporating wetting agents into concentrated dust compositions.

In some cases the active compounds are sufficiently soluble in common organic solvents such as kerosene or xylene so that they can be used directly as solutions in these solvents. Frequently, solutions of herbicides can be dispersed under superatmospheric pressure as aerosols. However, preferred liquid herbicidal compositions are emulsifiable concentrates, which comprise an active compound according to this invention and as the inert carrier, a solvent and an emulsifier. Such emulsifiable concentrates can be extended with water and/or oil to any desired concentration of active compound for application as sprays to the site of the weed infestation. The emulsifiers most commonly used in these concentrates are nonionic or mixtures of nonionic with anionic surface-active agents. With the use of some emulsifier systems an inverted emulsion (water in oil) can be prepared for direct application to weed infestation.

A typical herbicidal composition according to this invention is illustrated by the following example, in which the quantities are in parts by weight.

EXAMPLE 4

Preparation of a Dust

| Product of Example 1 | 10 |
|---|---|
| Powdered Talc | 90 |

The above ingredients are mixed in a mechanical grinder-blender and are ground until a homogeneous, free-flowing dust of the desired particle size is obtained. This dust is suitable for direct application to the site of the weed infestation.

The compounds of this invention can be applied as herbicides in any manner recognized by the art. One method for the control of weeds comprises contacting the locus of said weeds with a herbicidal composition comprising an inert carrier and as an essential active ingredient, in a quantity which is herbicidally toxic to said weeds, a compound of the present invention. The concentration of the new compounds of this invention in the herbicidal compositions will vary greatly with the type of formulation and the purpose for which it is designed, but generally the herbicidal compositions will comprise from about 0.05 to about 95 percent by weight of the active compounds of this invention. In a preferred embodiment of this invention, the herbicidal compositions will comprise from about 5 to about 75 percent by weight of the active compound. The compositions can also comprise such additional substances as other pesticides, such as insecticides, nematocides, fungicides, and the like; stabilizers, spreaders, deactivators, adhesives, stickers, fertilizers, activators, synergists and the like.

The compounds of the present invention are also useful when combined with other herbicides and/or defoliants, dessicants, growth inhibitors and the like in the herbicidal compositions heretobefore described.

These other materials can comprise from about 5% to about 95% of the active ingredients in the herbicidal compositions. Use of combinations of these other herbicides and/or defoliants, dessicants, etc. with the compounds of the present invention provide herbicidal compositions of the individual herbicides. The other herbicides, defoliants, dessicants and the plant growht inhibitors, with which the compounds of this invention can be used in the herbicidal compositions to control weeds, can include chlorophenoxy herbicides such as 2,4-D, 2,4,5-T, MCPA, MCPB, 4(2,4-DB), 2,4-DEB, 4-CPB, 4-XPP, 2,4,5-TB, 2,4,5-TES, 3,4,-DA, silvex and the like; carbamate, herbicides such as IPC, CIPC, swep, barban, BCPC, CEPC, CPPC, and the like; thiocarbamate and dithiocarbamate herbicides such as DCEC, methan sodium, EPTC, diallate, PEBC, perbulate, vernolate and the like; substituted urea herbicides such as norea, disuron, dichloral urea, chloroxuron, cycluron, fenuron, monuron, monuron TCA, diuron, linuron, molinuron, neburon, buturon; trimeturon and the like; symmetrical triazine, herbicides such as simazine, chlorazine, atraone, desmetryne, norazine, ipazine, prometryn atrazine, trietazine, simetone, prometone, propazine, ametryne, and the like; chloroacetamide herbicides such as alpha-chloro-N,n-dimethylacetamide, CDEA, CDAA, alpha-chloro-N-isopropylacetamide, 2-chloro-N-isopropyl-acetanilide, 4-(chloroacetyl)morpholine, 1-(chloracetyl)piperidine, and the like; chlorinated aliphatic acid herbicides such as TCA, dalapon, 2,3-dichloropropropionic acid, 2,2,3-TPA and the like; chlorinated benzoic acid and phenylacetic acid herbicides such as 2,3,6-TBA, 2,3,5,6-TBA, dicamba, tricamba, amiben, fenac, PBA, 2-methoxy-3,6-dichlorophenylacetic acid, 3-methoxy-2,6-dichlorophenylacetic acid, 2-methoxy-3,4,6-trichlorophenylacetic acid, 2,4-dichloro-3-nitrobenzoic acid and the like; and such compounds as aminotriazole, maleic hydrazide, phenyl mercuric acetate, endothal, biuret, technical chlordane, dimethyl 2,3,5,6-tetrachloroterephthalate, diquat, erbon, DNC, DNBP, dichlorobenil, DPA, diphenamid, dipropalin, trifluraline, solan, dicryl, merphos, DMPA, DSMA, MSMA, potassium azide, acrolein, benefin, bensulide, AMS, bromacil, 2-(3,4-dichlorophenyl)-4-methyl-1,2,4-oxadiazolidine, 3,5-dione, bromoxynil, cacodylic acid, DMA, DPMF, cypromid, DCB, DCPA, dichlone, diphenatril, DMTT, DNAP, EBEP, EXD, HCA, ioxynil, IPX, isocril, potassium cyanate, MAA, MAMA, MCPES, MCPP, MH, molinate, NPA, OCH paraquat, PCP, picloram, DPA, PCA, pyrichlor, sesone, terbacil, terbutol, TCBA, brominil, CP-50144, H-176-1, H-732, M-2091, planavin, dosium tetraborate, calcium cyanamid, DEF, ethyl xanthogen disulfide, sindone, sindone B, propanil and the like.

Such herbicides can also be used in the methods and composition of this invention in the form of their salts, esters, amides, and other derivatives whenever applicable to the particular patent compounds.

Weeds are undesirable plants growing where they are not wanted, having no economic value, and interfering with the production of cultivated crops, with the growing of ornamental plants, or with the welfare of livestock. Many types of weeds are known, including annuals such as pigweed, lambsquarter, foxtail, crabgrass, wild mustard, field pennycress, ryegrass, goose grass, chickweed, wild oats, velvet leaf, purselane, barnyard grass, smartweed, knotweed, cocklebur, wild buckwheat, kochia, medic corn cockle, ragweed, sowthistle, coffee-weed, croton, cuphea, dodder, fumitory, groundsel, hemp nettle, knowel, spurge, spurry, emex, jungle rice, pondweed, dog fennel, carpetweed, morning glory, bedstraw, ducksalad and naiad; biennials such as wild carrot, matricaria, wild barley, campion, chamomile, burdock, mullein, roundleaved mallow, bull thistle, hounds-tongue, moth mullein, and purple star thistle; or perennials such as white cockle, perennial ryegrass, quackgrass, Johnson grass, Canada thistle, hedge bindweed, Bermuda grass, sheep sorrel, curly dock, nutgrass, field chickweed, dandelion, campanula, field bindweed, Russian knapweed, mewquite, toadflax, yarrow, aster, gromwell, horsetail, ironweed, sesbania, bulrush, cattail and wintercrass.

Similarly, such weeds can be classified as broadleaf or grassy weeds. It is economically desirable to control the growth of such weeds without damaging beneficial plants or livestock.

The new compounds of this invention are particularly valuable for weed control because they are toxic to many species and groups of weeds while they are relatively nontoxic to many beneficial plants. The exact amount of compound required will depend on a variety of factors, including the hardiness of the particular weed species, weather, type of soil, method of application, the kind of beneficial plants in the same area, and the like. Thus, while the application of up to only about one or two ounces of active compound per acre may be sufficient for good control of a light infestation of weeds growing under adverse conditions, the application of ten pounds or more of active compound per acre may be required for good control of a dense infestation of hardy perennial weeds growing under favorable conditions.

The herbicidal toxicity of the new compounds of this invention can be illustrated by many of the established testing techniques known to the art, such as pre- and post-emergence testing.

The herbicidal activity of the compounds of this invention was demonstrated by experiments carried out for the pre-emergence control of a variety of weeds. In these experiments small plastic greenhouse pots filled with dry soil were seeded with the various weed seeds. Twenty-four hours or less after the seeding, the pots were sprayed with water until the soil was wet and the test compounds formulated as aqueous emulsions of acetone solutions containing emulsifiers were sprayed at the indicated concentrations on the surface of the soil.

After spraying, the soil containers were placed in the greenhouse and provided with supplementary heat as required and daily or more frequent watering. The plants were maintained under these conditions for a period of from 14 to 21 days, at which time the condition of the plant and the degrees of injury to the plants was rated on a scale of from 0 to 10, as follows: 0=no injury, 1, 2=slight injury, 3, 4=moderate injury, 5, 6=moderately severe injury, 7, 8, 9—severe injury, and 10=death. The effectiveness of these compounds is demonstrated by the following data:

| PRE-EMERGENCE HERBICIDAL DATA PRODUCT OF EXAMPLE 1 14 DAYS AFTER TREATMENT | | | | |
|---|---|---|---|---|
| LBS/ACRE | 1 | 0.5 | 0.25 | 0.125 |
| Wild Mustard | 10 | 10 | 10 | 0 |
| Bindweed | 7 | 3 | 5 | 0 |
| Pigweed | 10 | NE | 9 | 0 |
| Jimson Weed | 10 | 5 | NE | 0 |

-continued

PRE-EMERGENCE HERBICIDAL DATA
PRODUCT OF EXAMPLE 1
14 DAYS AFTER TREATMENT

| LBS/ACRE | 1 | 0.5 | 0.25 | 0.125 |
|---|---|---|---|---|
| Velvet Leaf | 10 | 2 | 0 | 0 |
| Morning Glory | 8 | 7 | 7 | 0 |
| Yellow Foxtail | 10 | 0 | 0 | 0 |
| Barnyard Grass | 9 | 1 | 0 | 0 |
| Johnson Grass | 10 | 8 | 2 | 0 |
| Quack Grass | 9 | 0 | 0 | 0 |
| Wild Oats | 6 | 2 | 0 | 0 |
| Crabgrass | 10 | 10 | NE | 9 |
| Sprangle Top | 9 | 6 | 9 | 0 |
| Cheat Grass | 0 | 0 | 0 | 0 |
| Sugar Beet | 10 | 10 | 10 | 7 |
| Soybean | 0 | 0 | 0 | 0 |
| Cotton | 8 | 3 | 0 | 0 |
| Pinto Bean | NE | NE | 9 | 0 |
| Alfalfa | 10 | 10 | 7 | 0 |
| Wheat | 5 | 3 | 0 | 0 |
| Rice | 0 | 0 | 0 | 0 |
| Sorghum | 8 | 7 | 4 | 0 |
| Corn | 5 | 0 | 0 | 0 |
| Oats | 3 | 1 | 0 | 1 |

PRE-EMERGENCE HERBICIDAL DATA
PRODUCT OF EXAMPLE 1
21 DAYS AFTER TREATMENT

| LBS/ACRE | 1 | 0.5 | 0.25 | 0.125 |
|---|---|---|---|---|
| Wild Mustard | 10 | 10 | 10 | 0 |
| Bindweed | 5 | 0 | 0 | 0 |
| Pigweed | 10 | NE | 10 | 0 |
| Jimson Weed | 10 | 0 | 0 | 0 |
| Velvet Leaf | 10 | 0 | 0 | 0 |
| Morning Glory | 6 | 0 | 0 | 0 |
| Yellow Foxtail | 10 | 0 | 0 | 0 |
| Barnyard Grass | 0 | 0 | 0 | 0 |
| Johnson Grass | 10 | 0 | 0 | 0 |
| Quack Grass | 10 | 0 | 0 | 0 |
| Wild Oats | 4 | 3 | 0 | 0 |
| Crabgrass | 10 | 10 | NE | 0 |
| Sprangle Top | 6 | 0 | 0 | 0 |
| Cheat Grass | 0 | 0 | 0 | 0 |
| Sugar Beet | 10 | 10 | 10 | 0 |
| Soybean | 0 | 0 | 0 | 0 |
| Cotton | 8 | 0 | 0 | 0 |
| Pinto Bean | 10 | 10 | 7 | 0 |
| Alfalfa | 10 | 10 | 0 | 0 |
| Wheat | 4 | 0 | 0 | 0 |
| Rice | 0 | 0 | 0 | 0 |
| Sorghum | 10 | 7 | 4 | 0 |
| Corn | 0 | 0 | 0 | 0 |
| Oats | 7 | 1 | 0 | 0 |

PRE-EMERGENCE HERBICIDAL DATA
PRODUCT OF EXAMPLE 2
14 DAYS AFTER TREATMENT

| LBS/ACRE | 1 | 0.5 | 0.25 | 0.125 |
|---|---|---|---|---|
| Wild Mustard | 10 | 10 | 9 | 1 |
| Bindweed | 9 | 8 | 9 | 0 |
| Pigweed | 10 | 10 | 5 | 0 |
| Jimson Weed | 10 | 10 | 5 | 0 |
| Velvet Leaf | 10 | 9 | 5 | 0 |
| Morning Glory | 10 | 9 | 1 | 0 |
| Yellow Foxtail | 10 | 5 | 0 | 0 |
| Barnyard Grass | 10 | 10 | 1 | 0 |
| Johnson Grass | 10 | 9 | 8 | 0 |
| Quack Grass | 10 | 9 | 5 | 0 |
| Wild Oats | 9 | 7 | 1 | 0 |
| Crabgrass | 10 | NE | 10 | 10 |
| Sprangle Top | 10 | 10 | 0 | 0 |
| Cheat Grass | 2 | 1 | 0 | 0 |
| Sugar Beet | 10 | 10 | 10 | 8 |
| Soybean | 9 | 7 | 3 | 0 |
| Cotton | NE | 9 | 3 | 0 |
| Pinto Bean | NE | NE | NE | 8 |
| Alfalfa | 10 | 10 | 10 | 10 |
| Wheat | 10 | 9 | 5 | 0 |
| Rice | 9 | 8 | 3 | 0 |
| Sorghum | 10 | 9 | 8 | 2 |
| Corn | 9 | 7 | 5 | 0 |
| Oats | 10 | 5 | 1 | 0 |

PRE-EMERGENCE HERBICIDAL DATA
PRODUCT OF EXAMPLE 2
21 DAYS AFTER TREATMENT

| LBS/ACRE | 1 | 0.5 | 0.25 | 0.125 |
|---|---|---|---|---|
| Wild Mustard | 10 | 10 | 0 | 0 |
| Bindweed | 7 | 6 | 5 | 0 |
| Pigweed | 10 | 10 | 0 | 0 |
| Jimson Weed | 10 | 10 | 0 | 0 |
| Velvet Leaf | 10 | 2 | 0 | 0 |
| Morning Glory | 10 | 9 | 0 | 0 |
| Yellow Foxtail | 10 | 0 | 0 | 0 |
| Barnyard Grass | 10 | 10 | 0 | 0 |
| Johnson Grass | 10 | 8 | 7 | 1 |
| Quack Grass | 10 | 9 | 5 | 0 |
| Wild Oats | 10 | 2 | 5 | 0 |
| Crabgrass | 10 | NE | 10 | 10 |
| Sprangle Top | 10 | 10 | 0 | 0 |
| Cheat Grass | 0 | 0 | 0 | 0 |
| Sugar Beet | 10 | 10 | 10 | 8 |
| Soybean | 7 | 3 | 0 | 0 |
| Cotton | NE | 5 | 0 | 0 |
| Pinto Bean | NE | NE | 8 | 8 |
| Alfalfa | 10 | 10 | 10 | 10 |
| Wheat | 10 | 10 | 0 | 0 |
| Rice | 10 | 7 | 2 | 0 |
| Sorghum | 10 | 10 | 8 | 6 |
| Corn | 6 | 1 | 0 | 0 |
| Oats | 10 | 7 | 5 | 0 |

PRE-EMERGENCE HERBICIDAL DATA
PRODUCT OF EXAMPLE 3
14 DAYS AFTER TREATMENT

| LBS/ACRE | 1 | 0.5 | 0.25 | 0.125 |
|---|---|---|---|---|
| Wild Mustard | 10 | 10 | 10 | 9 |
| Bindweed | 10 | 9 | 7 | 6 |
| Pigweed | 10 | 10 | 10 | 10 |
| Jimson Weed | 10 | 10 | 10 | 6 |
| Velvet Leaf | — | — | — | — |
| Morning Glory | 10 | 10 | 8 | 2 |
| Yellow Foxtail | 6 | 5 | 3 | 1 |
| Barnyard Grass | 9 | 9 | 5 | 2 |
| Johnson Grass | 10 | 10 | 9 | 7 |
| Quack Grass | 6 | 4 | 3 | 2 |
| Wild Oats | 3 | 2 | 1 | 1 |
| Crabgrass | 7 | 5 | 2 | 0 |
| Sprangle Top | 9 | 6 | 5 | 5 |
| Cheat Grass | 3 | 2 | 2 | 1 |
| Sugar Beet | 10 | 10 | 10 | 10 |
| Cotton | 9 | 9 | 9 | 8 |
| Soybean | 5 | 5 | 3 | 2 |
| Pinto Bean | 9 | 8 | 6 | 6 |
| Alfalfa | 10 | 10 | 10 | 9 |
| Sorghum | 9 | 8 | 6 | 4 |
| Wheat | 5 | 4 | 2 | 2 |
| Rice | 2 | 2 | 2 | 1 |
| Corn | 6 | 5 | 3 | 3 |
| Oats | 6 | 2 | 1 | 1 |

The herbicidal activity of the compounds of this invention was also demonstrated by experiments carried out for the post-emergence control of a variety of weeds. In these experiments the compounds to be tested were formulated as aqueous emulsions and sprayed at the indicated dosage on the foliage of the various weed species that have attained a prescribed size. After spraying, the plants were placed in a greenhouse and watered daily or more frequently. Water was not applied to the foliage of the treated plants. The severity of the injury was determined 14 to 21 days after treatment and was rated on the scale of from 0 to 10 heretobefore described. The effectiveness of these compounds is demonstrated by the following data:

| POST-EMERGENCE HERBICIDAL DATA PRODUCT OF EXAMPLE 1 | | | | |
|---|---|---|---|---|
| LBS/ACRE | 1 | 0.5 | 0.25 | 0.125 |
| Wild Mustard | 10 | 10 | 10 | 10 |
| Bindweed | 8 | 8 | 4 | 0 |
| Pigweed | — | — | 10 | 10 |
| Jimson Weed | 10 | 10 | 10 | 10 |
| Velvet Leaf | 10 | 10 | 10 | 10 |
| Morning Glory | 9 | 7 | 7 | 0 |
| Yellow Foxtail | 10 | 7 | 0 | 0 |
| Barnyard Grass | 5 | 0 | 0 | 0 |
| Johnson Grass | 9 | 7 | 2 | 0 |
| Quack Grass | 9 | 3 | 1 | 0 |
| Wild Oats | 5 | 1 | 0 | 0 |
| Crabgrass | 0 | 0 | 0 | 0 |
| Sprangle Top | 10 | 0 | 0 | 0 |
| Cheat Grass | 0 | 0 | 0 | 0 |
| Sugar Beets | 10 | 10 | 10 | 10 |
| Cotton | 10 | 10 | 10 | 10 |
| Soybean | 0 | 0 | 0 | 0 |
| Pinto Bean | 10 | 10 | 10 | 10 |
| Alfalfa | 10 | 10 | 10 | 9 |
| Sorghum | 7 | 1 | 0 | 0 |
| Wheat | 2 | 1 | 0 | 0 |
| Rice | 2 | 0 | 0 | 0 |
| Corn | 0 | 0 | 0 | 0 |
| Oats | 4 | 0 | 0 | 0 |

| POST-EMERGENCE HERBICIDAL DATA PRODUCT OF EXAMPLE 2 | | | | |
|---|---|---|---|---|
| LBS/ACRE | 1 | 0.5 | 0.25 | 0.125 |
| Wild Mustard | 10 | 10 | 10 | 10 |
| Bindweed | 10 | 10 | 10 | 10 |
| Pigweed | — | — | 10 | 10 |
| Jimson Weed | 10 | 10 | 10 | 10 |
| Velvet Leaf | 10 | 10 | 10 | 10 |
| Morning Glory | 10 | 10 | 7 | 10 |
| Yellow Foxtail | 10 | 10 | 9 | 5 |
| Barnyard Grass | 10 | 10 | 10 | 4 |
| Johnson Grass | 10 | 10 | 8 | 10 |
| Quack Grass | 10 | 10 | 10 | 1 |
| Wild Oats | 10 | 7 | 1 | 0 |
| Crabgrass | 10 | 10 | 7 | 8 |
| Sprangle Top | 10 | 10 | 10 | 10 |
| Cheat Grass | 9 | 1 | 0 | 0 |
| Sugar Beets | 10 | 10 | 10 | 10 |
| Cotton | 10 | 10 | 10 | 10 |
| Soybean | 10 | 5 | 2 | 2 |
| Pinto Bean | 10 | 10 | 10 | 10 |
| Alfalfa | 10 | 10 | 10 | 10 |
| Sorghum | 10 | 10 | 8 | 8 |
| Wheat | 10 | 10 | 10 | 7 |
| Rice | 10 | 9 | 6 | 10 |
| Corn | 10 | 3 | 3 | 0 |
| Oats | 10 | 7 | 1 | 1 |

| POST-EMERGENCE HERBICIDAL DATA PRODUCT OF EXAMPLE 3 | | | | |
|---|---|---|---|---|
| LBS/ACRE | 1 | 0.5 | 0.25 | 0.125 |
| Wild Mustard | 10 | 10 | 10 | 9 |
| Bindweed | 10 | 9 | 7 | 6 |
| Pigweed | 10 | 10 | 10 | 10 |
| Jimson Weed | 10 | 10 | 10 | 6 |
| Velvet Leaf | — | — | — | — |
| Morning Glory | 10 | 10 | 8 | 2 |
| Yellow Foxtail | 6 | 5 | 3 | 1 |
| Barnyard Grass | 9 | 9 | 5 | 2 |
| Johnson Grass | 10 | 10 | 9 | 7 |
| Quack Grass | 6 | 4 | 3 | 2 |
| Wild Oats | 3 | 2 | 1 | 1 |
| Crabgrass | 7 | 5 | 2 | 0 |
| Sprangle Top | 9 | 6 | 5 | 5 |
| Cheat Grass | 3 | 2 | 2 | 1 |
| Sugar Beets | 10 | 10 | 10 | 10 |
| Cotton | 9 | 9 | 9 | 8 |
| Soybean | 5 | 5 | 3 | 2 |
| Pinto Bean | 9 | 8 | 6 | 6 |
| Alfalfa | 10 | 10 | 10 | 9 |
| Sorghum | 9 | 8 | 6 | 4 |
| Wheat | 5 | 4 | 2 | 2 |
| Rice | 2 | 2 | 2 | 1 |
| Corn | 6 | 5 | 3 | 3 |
| Oats | 6 | 2 | 1 | 1 |

We claim:
1. A compound of the formula:

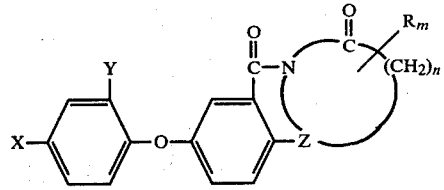

wherein X is halogen or trifluoromethyl; Y is hydrogen, halogen or cyano; Z is halogen, cyano or nitro; R is $C_1$–$C_6$ alkyl; m is an integer from 0 to 6 and n is an integer from 3 to 5.
2. A compound of claim 1 wherein Z is nitro.
3. A compound of claim 2 wherein X is trifluoromethyl.
4. A compound of claim 2 wherein m is 0.
5. A compound of claim 4 wherein n is 3.
6. A compound of claim 4 wherein n is 4.
7. A compound of claim 4 wherein n is 5.
8. A compound of claim 1, 1-[3-(2-Chloro-4-Trifluoromethylphenoxy)-6-Nitrobenzoyl] Hexamethyleneimin-2-one.
9. The compound of claim 1, 1-[3-(2-Chloro-4-Trifluoromethylphenoxy)-6-Nitrobenzoyl] Pyrrolidin-2-one.
10. The compound of claim 1, 1-[3-(2-Chloro-4-Trifluoromethylphenoxy)-6-Nitrobenzoyl] Piperidin-2-one.
11. A herbicidal composition comprising an inert carrier and, as an essential active ingredient in a quantity toxic to weeds, a compound of claim 1.
12. A method of controlling weeds which comprises contacting said weeds with a herbicidal composition comprising an inert carrier and, as an essential active ingredient in a quantity toxic to weeds, a compound of claim 1.

* * * * *